(12) United States Patent
Audie

(10) Patent No.: US 7,739,091 B2
(45) Date of Patent: Jun. 15, 2010

(54) METHOD FOR ESTIMATING PROTEIN-PROTEIN BINDING AFFINITIES

(75) Inventor: Joseph Audie, Meriden, CT (US)

(73) Assignee: The Research Foundation of State University of New York, Albany, NY (US)

( * ) Notice: Subject to any disclaimer, the term of this patent is extended or adjusted under 35 U.S.C. 154(b) by 125 days.

(21) Appl. No.: 11/726,266

(22) Filed: Mar. 21, 2007

(65) Prior Publication Data

US 2007/0224646 A1    Sep. 27, 2007

Related U.S. Application Data

(60) Provisional application No. 60/785,232, filed on Mar. 23, 2006, provisional application No. 60/878,217, filed on Jan. 3, 2007.

(51) Int. Cl.
*G06G 7/58* (2006.01)
(52) U.S. Cl. ...................................................... 703/11
(58) Field of Classification Search ........................ None
See application file for complete search history.

(56) References Cited

U.S. PATENT DOCUMENTS

| | | | |
|---|---|---|---|
| 5,600,571 A | 2/1997 | Friesner et al. | |
| 6,671,628 B2 | 12/2003 | Hurst | |
| 6,741,937 B2 | 5/2004 | Waldman et al. | |
| 6,823,267 B2 | 11/2004 | Freire | |
| 6,969,763 B1 | 11/2005 | Ecker et al. | |
| 6,970,790 B2 | 11/2005 | Kita et al. | |
| 2003/0045710 A1 * | 3/2003 | Bruice et al. | 540/456 |
| 2003/0167136 A1 | 9/2003 | Hurst | |
| 2004/0034481 A1 | 2/2004 | Hurst | |
| 2004/0073375 A1 | 4/2004 | Hurst | |
| 2004/0096897 A1 | 5/2004 | Zhou et al. | |
| 2004/0204862 A1 | 10/2004 | Wainer et al. | |
| 2005/0033522 A1 | 2/2005 | Wainer et al. | |
| 2005/0114035 A1 | 5/2005 | Robinson et al. | |
| 2005/0119834 A1 | 6/2005 | Kita et al. | |
| 2005/0119835 A1 | 6/2005 | Kita et al. | |
| 2005/0119837 A1 | 6/2005 | Prakash et al. | |
| 2005/0123993 A1 | 6/2005 | Brunner et al. | |
| 2005/0170379 A1 | 8/2005 | Kita et al. | |
| 2005/0214788 A1 | 9/2005 | Che | |
| 2006/0136139 A1 | 6/2006 | Elcock et al. | |
| 2007/0038379 A1 | 2/2007 | Vaidehi et al. | |

OTHER PUBLICATIONS

Rognan et al., Journal of Medicinal Chemistry, 1999, vol. 42, No. 22, p. 4650-4658.*
Crowley et al., Proteins: Structure, Function, and Bioinformatics, 2004, vol. 55, p. 603-612.*
Labriola-Tompkins et al., Proc. Natl. Acad. Sci., 1991, vol. 88, p. 11182-11186.*
Zou et al., J. Am. Chem. Soc., 1999, vol. 121, No. 35, p. 8033-8043.*
Jones et al., Proc. Natl. Acad. Sci, 1996, vol. 93, p. 13-20.*

* cited by examiner

*Primary Examiner*—Shubo (Joe) Zhou
*Assistant Examiner*—Pablo Whaley
(74) *Attorney, Agent, or Firm*—Todd E. Garabedian; Jay H. Anderson; Wiggin and Dana LLP

(57) ABSTRACT

The present invention is directed to a method of predicting the binding affinity between a first molecular entity and a second molecular entity. The method includes (1) calculating the free energy of binding $\Delta G_{bind}$ between the first molecular entity and the second molecular entity according to the equation (17):

$$\Delta G_{bind} = -0.82 \Delta X_{+/-} + 0.064 \Delta X_{c/s} - 0.6 X_{sb} - 0.93 X_{hb} - 0.0007 X_{gap} - 0.06 \Delta X_{tor} - 0.36 \quad (17)$$

where
$X_{+/-}$ is the total number of exposed charged groups;
$X_{c/s}$ is the total number of exposed hydrophobic groups;
$X_{sb}$ is the total number of salt bridges;
$X_{hb}$ is the total number of hydrogen bonds;
$X_{gap}$ is the gap volume at the interface of the first molecular entity and the second molecular entity;
$X_{tor}$ is the total number of exposed side chain torsions;
and where $\Delta$ refers to the difference between the bound and unbound states; and (2) evaluating the free energy of binding to predict the binding affinity between the first and second molecular entities.

11 Claims, 4 Drawing Sheets

METHOD FOR ESTIMATING PROTEIN-PROTEIN BINDING AFFINITIES

CROSS-REFERENCE TO RELATED APPLICATIONS

This application claims the benefit of U.S. Provisional Application Ser. No. 60/785,232 filed Mar. 23, 2006 and U.S. Provisional Application Ser. No. 60/878,217 filed Jan. 3, 2007.

STATEMENT OF GOVERNMENT SUPPORT

This invention was made in part with government support under grant number GM NIH-53132 from the National Institutes of Health. The government has certain rights in this invention.

BACKGROUND OF THE INVENTION

1. Field of the Invention

The present invention is directed to methods of estimating protein-protein or protein-peptide binding affinities, and more particularly to methods of estimating protein-protein or protein-peptide binding affinities using free energy functions.

2. Description of the Related Art

A free energy function can be defined as any mathematical expression that relates macroscopic free energy changes to microscopic or molecular properties. Free energy functions can be used to explain and predict the affinity of a ligand for a protein and to score and discriminate between native and non-native binding modes. However, there is a natural tension between developing a function fast enough to solve the scoring problem but rigorous enough to explain and predict binding affinities.

There is a need for computational methods to explain and predict free energy changes for biophysical and biochemical processes (Ajay et al. (1995) J. Med. Chem. 38(26):4953-4967; Gilson et al., (1997) Biophys. J. 72(3):1047-1069; Guerois et al., (2002) J. Mol. Biol. 320(2):369-387; Vajda et al., (1997) Curr. Opin. Struct. Biol. 7(2):222-228). An important class of biophysical phenomena is that of non-covalent protein-protein interactions. Such vital activities as cellular growth, self-reproduction, and cellular communication are supported by a byzantine network of signaling cascades and metabolic pathways which rely on the coordinated and tightly regulated activities of interacting proteins, thus making protein-protein interactions attractive targets for therapeutic intervention (Feller et al., (2006) Curr. Pharm. Des. 12(5): 529-548). The ability to estimate the free energy changes that control protein-protein associations will allow us to predict whether these interactions can occur under particular environmental conditions.

Specifically, free energy functions are needed to solve three problems: (1) predicting and explaining experimentally determinable protein-protein dissociation constants; (2) predicting and explaining how different mutations affect those equilibrium constants; and (3) accurately scoring and ranking the binding poses generated by protein-protein docking algorithms (Guerois et al., (2002) J. Mol. Biol. 320(2):369-387; Halperini et al., (2002) Proteins 47(4):409-443; Smith et al., (2002) Curr. Opin. Struct. Biol. 12(1):28-35; Weng et al., (1997) Protein Sci. 6(9):1976-1984). Ideally, the function should also be transferable; it should work equally well for a diverse and large number of proteins. Given the biological and clinical importance of free energy functions and the nature of the scientific challenge, a considerable amount of effort has been devoted to researching free energy methods (Ajay et al., supra; Guerois et al., supra; Horton et al., (1992) Protein Sci. 1(1):169-181; Jackson et al., (1988) J. Mol. Biol. 276(1):265-285; Krystek et al., (1993) J. Mol. Biol. 234(3): 661-679; Ma et al., (2002) Protein Eng. 15(8):677-681; Rognan et al., J. Med. Chem. 42(22):4650-4658; Schapira et al., (1999) J. Mol. Recognit. 12(3):177-190; Vajda et al. supra; Weng et al., supra; Xu et al., (1997) J. Mol. Biol. 265(1):68-84; Zhang et al., (2005) J. Med. Chem. 48(7): 2325-233; Zhou et al., (1998) Fold. Des. 3(6):513-522). Despite its importance, the development of a function to solve all three problems remains elusive. In part, this is because theoretical validity and physical meaningfulness tend to exclude computational efficiency (Gilson et al., supra; Rognan et al., (1999) J. Med. Chem. 42(22):4650-4658).

Computer-based modeling of interactions between molecular entities using various energy functions are the subject of several patents and patent applications as follows:

U.S. Pat. No. 6,970,790 discloses a method and apparatus for an analysis of molecular combinations featuring two or more molecular subsets, wherein either one or both molecular subsets are from a plurality of molecular subsets selected from a molecule library, based on computation of the electrostatic affinity of the system via utilization of a basis expansion representing charge density and electrostatic potential functions associated with the first and second molecular subsets in a coordinate system.

U.S. Pat. No. 6,823,267 discloses a computer-assisted method for creating and displaying a model of a molecule in which residues that are affected by the binding of a ligand to the molecule are highlighted, making it possible to trace the path of propagation of a binding signal through the molecule.

U.S. Pat. No. 6,741,937 discloses methods and systems of predicting binding affinity between a ligand and a receptor. In one embodiment, the predicted binding affinity (pKj) is determined by at least using a formula $$pKj = C0 + C1*vdW + C2*Att\_pol + C3*(Att\_pol*Att\_pol + Rep\_pol*Rep\_pol)$$

where vdW represents the van der Waals interaction energy between the ligand and the receptor; Att_pol represents the surface area of the ligand forming complimentary polar interactions with the receptor; and Rep_pol represents the surface area of the ligand forming uncomplimentary polar interactions with the receptor.

U.S. Pat. No. 6,671,628 discloses methods which may be implemented in computer systems for screening a database of candidate molecules to determine whether any particular subset of candidate molecules may be docked to a target molecule. These methods determine the force field of a target molecule only once and may be used for screening a large number of candidate molecules.

U.S. Pat. No. 5,600,571 discloses a method for determining the most stable tertiary structure of a protein having a known primary structure which comprises the steps of (a) producing a reduced representation of the protein by assigning to the protein (i) all secondary structural motifs present therein and (ii) all $\phi$ and $\Phi$ dihedral angles for the amino acid residues present therein; (b) determining which conformations of the reduced representation are physically permissible, so as to determine which conformations of the protein are physically permissible; and (c) determining which of the physically permissible conformations of the protein possesses the lowest free energy, so as to thereby determine the most stable tertiary structure of the protein.

U.S. Patent Application Publication No. US 2007/0038379 discloses a hierarchical protocol using multiscale molecular dynamics and molecular modeling methods to predict the structure of G-Protein Coupled Receptors. The protocol features a combination of coarse grain sampling methods, such as hydrophobicity analysis, followed by coarse grain molecular dynamics and atomic level molecular dynamics, including accurate continuum solvation, to provide a fast and accurate procedure for predicting GPCR tertiary structure.

U.S. Patent Application Publication No. US 2006/0136139 discloses computational methods for identifying the protein receptors likely to bind a drug, which can provide accurate predictions of the drug's ability to bind to each homologue of the receptor using energy minimization functions.

U.S. Patent Application Publication No. 2005/0214788 discloses methods and systems for modeling molecular systems or other physical systems using scaling optimization. The disclosed method includes predicting a conformation of a ligand inside a binding site using a computer system by the steps of representing a candidate ligand by topological clusters, and scaling conformational and/or orientational degrees of freedom or their corresponding derivatives iteratively while applying one or more optimization and/or scoring and/or energy determination functions.

U.S. Patent Application Publication No. 2005/0123993 discloses methods for determining the affinity between polypeptide amino acid residues and one or more molecular fragments, and for using the affinity values to aid in drug design including a computer simulation which calculates the interaction energy between a polypeptide and at least one molecular fragment.

U.S. Patent Application Publication No. 2005/0119835 discloses a method and apparatus for analysis of molecular combinations featuring two or more molecular subsets. The computational method estimates the electrostatic affinity of the system via utilization of a basis expansion representing charge density and electrostatic potential functions associated with the first and second molecular subsets in a coordinate system. An electrostatic affinity, representing a correlation of the charge density and electrostatic potential functions of the first and second molecular subsets, is computed via suitable application of translation and rotation operators to the basis expansion coefficients over a sequence of different sampled configurations for the molecular combination.

In spite of the above technology, there is a need in the art for computational methods to explain and predict free energy changes for biophysical and biochemical processes. The present invention is believed to be an answer to that need.

SUMMARY OF THE INVENTION

In one aspect, the present invention is directed to a method of predicting the binding affinity between a first molecular entity and a second molecular entity, comprising the steps of: (1) calculating the free energy of binding $\Delta G_{bind}$ between the first molecular entity and the second molecular entity according to the equation (17):

$$\Delta G_{bind} = -0.82\Delta X_{+/-} + 0.064\Delta X_{c/s} - 0.6 X_{sb} - 0.93 X_{hb} - 0.0007 X_{gap} - 0.06\Delta X_{tor} - 0.36 \quad (17)$$

wherein $X_{+/-}$ is the total number of exposed charged groups;

$X_{c/s}$ is the total number of exposed hydrophobic groups;

$X_{sb}$ is the total number of salt bridges;

$X_{hb}$ is the total number of hydrogen bonds;

$X_{gap}$ is the gap volume at the interface of the first molecular entity and the second molecular entity;

$X_{tor}$ is the total number of exposed side chain torsions;

wherein $\Delta$ refers to the difference between the bound and unbound states; and (2) evaluating the free energy of binding to predict the binding affinity between the first molecular entity and the second molecular entity.

These and other aspects will become apparent upon reading the following description of the invention.

BRIEF DESCRIPTION OF THE FIGURES

The invention will be better understood when taken in conjunction with the Figures in which.

DETAILED DESCRIPTION OF THE INVENTION

Figure 1:
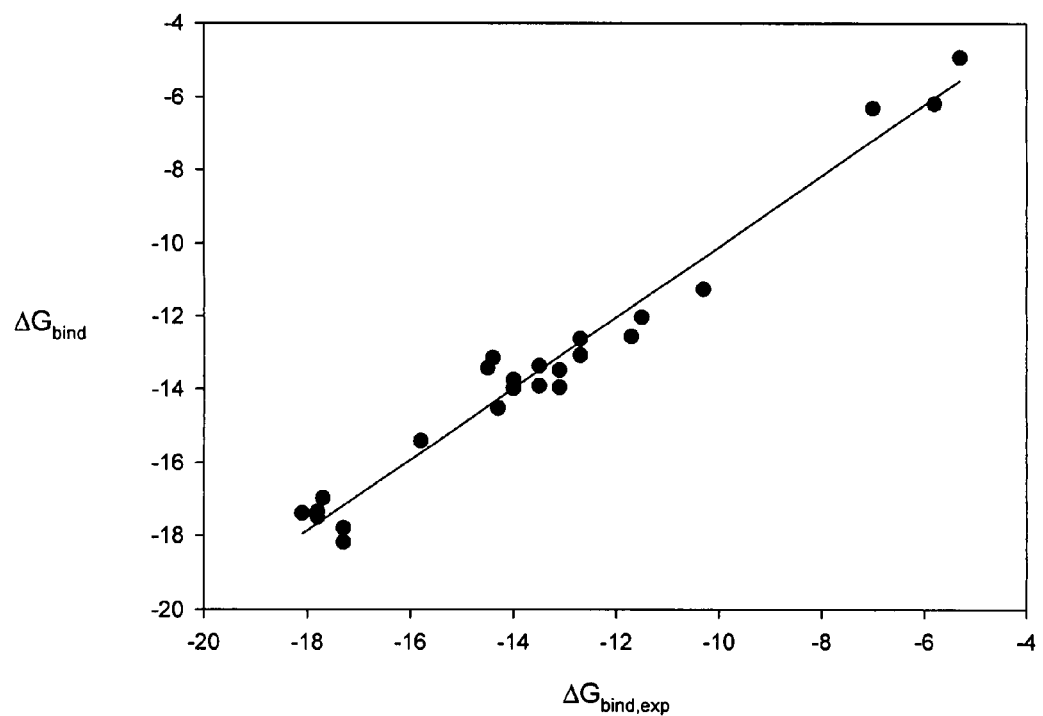
FIG. 1 shows experimental training set binding affinities ($\Delta G_{bind,exp}$) versus binding affinities estimated using Eq. (17) (kcal·mol$^{-1}$); see Table 1 for data for all 24 training set complexes; $r^2$=0.97; rmsd=0.62 kcal·mol$^{-1}$; $q^2$=0.91.

Sophisticated and computationally expensive methods are often thought to be required to fully explain and accurately predict mutant and wild type binding affinities, and to develop transferable methods. On the other hand, many protein design problems, especially the protein-protein docking problem, require simple and fast free energy functions that can successfully discriminate native-like binding modes from non-native ones. The present invention, termed PPIscore (protein-protein interaction score), is an empirical free energy function that is simple and fast, and thus suitable for the docking problem, yet with a solid basis in physical theory and experiment that allow for its use in predicting and rationalizing mutant and wild type binding affinities in terms of molecular properties. Thus, PPIscore may be implemented as part of a method of predicting the binding affinity between molecular entities such as proteins and/or peptides, in both wild type and mutant states.

The present disclosure suggests a coherent, unified, physically plausible and testable picture of protein-protein and protein-peptide association reactions. According to this picture of binding, protein-protein (peptide) interfaces are structured so as to minimize the interchain Van der Waals (vdw) and dipolar (diplr) energy, and in doing so to offset the loss of favorable vdw and hydrogen bonding interactions with water. While the burial of apolar groups or the hydrophobic effect is predicted to weakly favor binding, the quantum-mechanical component of receptor-ligand hydrogen bonds appears to play a key role in stabilizing protein-protein complexes. Long range, water mediated receptor-ligand interactions are also predicted to favor complex formation. The primary forces opposing association are charge group burial and the immobilization of side chain (and main chain torsions in the case of peptide ligands) torsions at the receptor-ligand interface, although the latter appears to be less unfavorable than previously thought. Surprisingly, binding induced changes in the free energy of translation and rotation appear to make a negligible contribution to binding. Finally, depending on their number and nature salt bridges can be overall stabilizing or destabilizing.

In sum, the method of the present invention, which is based on physical principles, can predict and explain, within well-defined limits, the free energy of association for a large number of protein complexes. Moreover, preliminary results suggest the method of the present invention can be used to discriminate native-like binding poses from non-native ones. Because of its algorithmic simplicity and speed, it is believed that the method of the present invention can be applied to numerous protein-protein design and discovery problems, particularly the docking problem.

In the following analysis, an a priori derivation of the PPIscore function from fundamental principles is given and it is shown and that the final regression equation accurately models the training set binding data in a statistically significant manner. It is also shown that each physical descriptor is a suitable estimator of its corresponding thermodynamic term. Thus, the method is shown to explain protein-protein binding affinities. In addition, the method of the present invention can predict wild type (WT) and mutant binding affinities. This feature of the invention was tested by leave-one-out cross validation and by blind prediction on WT and mutant test sets, with encouraging results. The ability of the method to accurately predict binding for such a diverse test set further suggests the function is transferable. The ability of the method of the invention to identify native and native-like binding modes against decoys for 9 protein-protein and protein-peptide complexes is shown with good results and suggests the function can be used to discriminate native from non-native binding modes.

Basic Thermodynamic Principles and Key Simplifying Assumptions

From the perspective of thermodynamics, protein-protein or receptor-ligand binding reactions can be described in terms of three macroscopic states (Ajay et al., supra; Gilson et al.; supra)

$$R(N)+L(N) \rightarrow RL \quad (1)$$

where R(N) refers to a 1M aqueous solution of native-state (free energy minimum structure) receptor, with standard state free energy $G_{R(N)}$; L(N) refers to a 1M aqueous solution of native-state ligand, with standard state free energy $G_{L(N)}$; and RL refers to a 1M aqueous solution of receptor-ligand complexes, with standard state free energy $G_{RL}$. The association reaction represented by Eq. (1) can be conceptualized in terms of two coupled (standard state) reactions, an isomerization reaction ($\Delta G_{isomer}$) and a binding reaction ($\Delta G_{bind}$), $$R(N)+L(N) \rightarrow R+L \, \Delta G_{isomer} \quad (1a)$$

$$R+L \rightarrow RL \, \Delta G_{bind} \quad (1b)$$

where isomerization is from the free ligand and receptor native states to their respective "strained" binding conformations. Complex formation is then assumed to proceed between "rigid-bodies" as depicted in the binding reaction (Eq. (1b)). This model allows for the experimental determination of the association constant, $K_a$, and the standard state free energy of association, $\Delta G_{association}$, in terms of $\Delta G_{isomer}$ and $\Delta G_{bind}$, $$\Delta G_{association} = G_{RL} - G_{R(N)} - G_{L(N)} = -RT \ln(K_a) = \Delta G_{isomer} + \Delta G_{bind} \quad (2)$$

In all that follows, it is assumed that $\Delta G_{isomer} = \Delta H_{isomer} - T \Delta S_{isomer} \approx 0$. This simplification (i.e. rigid body binding) is justified for binding reactions that involve only minor conformational changes and allows us to substitute the co-crystallized coordinates of the receptor and ligand (R and L) for their unbound coordinates (R(N) and L(N)) (Schapira et al., (1999) J Mol Recognit 12(3):177-190; Vajda et al., (1994) Biochemistry 33(47):13977-13988). Importantly, a relatively large and diverse class of protein-protein and protein-peptide associations entails only minor conformational changes (Mintseris et al., (2005) Proteins 60(2):214-216).

To rigorously predict $\Delta G_{bind}$ from the molecular properties of R, L, and RL, one needs to calculate the partition functions ($Q_R$, $Q_L$, $Q_{RL}$) for R, L and RL from an explicit consideration of the molecular ensembles for R, L, and RL and with an explicit solvent model. This approach, however, is too computationally demanding. A simpler method is to assume two-state binding and identify each macroscopic state with a single, experimentally determined molecular structure (Brem et al., (1999) Protein Sci. 8(5):1134-1143; Gilson et al., supra) and then derive a statistical relationship between the molecular properties of each structure and $\Delta G_{bind}$ (Ajay et al., supra; Horton et al., supra; Ma et al., supra; Xu et al., supra). Finally, because the pressure-volume work contribution is negligible, it is possible to equate the enthalpy change with energy change, $\Delta H \approx \Delta E$ (Ajay et al., supra).

Formal Derivation of the Master Thermodynamic Equation

The magnitude and sign for $\Delta G_{bind}$ arises from changes in the entropy and energy of binding. It is assumed that the change in energy can be explicitly estimated from the crystal coordinates of R, L, and RL, while the change in entropy (~the ensemble sizes for R, L, and RL) can be estimated implicitly from the same coordinate set. The total energy of the free (f) state can be given in terms of the energy of the unbound receptor (r), unbound ligand (l), solvent (w) and their respective interactions (Vajda et al., supra).

$$E^f = E^f_r + E^f_l + E^f_{r,tr} + E^f_{l,tr} + E^f_w + E^f_{r-w} + E^f_{l-w} \quad (3)$$

In Eqn. 3, $E^f_r$ and $E^f_l$ refer to the intramolecular energy of the receptor and ligand; $E^f_{r,tr}$ and $E^f_{l,tr}$ refer to the translational and rotational energy of the receptor and ligand; $E^f_w$ refers to the self-energy of water; and $E^f_{r-w}$ and $E^f_{l-w}$ refer to the intermolecular energy of interaction between the receptor and water (r-w) and the ligand and water (l-w), respectively. Following complex formation, the total energy of the bound (b) state is given by $$E^b = E^b_r + E^b_l + E^b_{r-l} + E^b_{r-w-l} + E^b_{(rl),tr} + E^b_w + E^b_{(rl)-w} \quad (4)$$

where $E^b_r$ and $E^b_l$ refer to the intramolecular energy of the bound receptor and ligand; $E^b_{r-l}$ is the energy of interaction that arises from direct receptor-ligand contacts; $E^b_{r-w-l}$ refers to the energy of interaction between water bridged receptor-ligand contacts; $E^b_{(rl),tr}$ designates the translational and rotational energy of the complex; $E^b_w$ refers to the self-energy of water in the bound state; and $E^b_{(rl)-w}$ refers to the interaction energy between the receptor-ligand complex and water. Eq. (4) minus Eq. (3) gives the binding induced change in energy, $$\Delta E_{bind} = (E^b_r - E^f_r) + (E^b_l - E^f_l) + E^b_{r-l} + E^b_{r-w-l} + \\ (E^b_{(rl),tr} - E^f_{r,tr} - E^f_{l,tr}) + (E^b_{(rl)-w} - E^f_{r-w} - E^f_{l-w}) + (E^b_w - E^f_w) \quad (5)$$

Rigid-body binding implies that the first two terms in Eq. 5 (Ajay et al., supra; Horton et al., supra; Krystek et al., supra;

Schapira et al., supra; Vajda et al. (1997), supra; Vadja et al., (1994), supra; Weng et al., supra) can be neglected, giving Eqn. 6.

$$\Delta E_{bind} = E^b_{r-l} + E^b_{r-w-l} + \Delta E_{tr} + \Delta E_{(rl)-w} + (E^b_w - E^f_w) \quad (6)$$

where $\Delta E_{tr} = E^b_{(rl),tr} - E^f_{r,tr} - E^f_{l,tr}$ and $\Delta E_{(rl)-w} = E^b_{(rl)-w} - E^f_{r-w} - E^f_{l-w}$. The receptor-ligand and water interaction terms can be decomposed into Van der Waals (vdw), ionic (ion), quantum (qm) and dipolar (diplr) contributions (at the interface this includes dipole-dipole and dipole-ion interaction energies). Hydrogen bonds are specified by the presence of dipolar (or ionic) and quantum mechanical (quasi-covalent) interactions, $E_{hb} = E_{diplr(ionic)} + E_{qm}$. The ionic and dipolar interactions can exist in the absence of hydrogen bonds; the quantum interactions cannot. Also, while the partitioning scheme makes explicit provisions for receptor-ligand qm interactions, any receptor-water, ligand-water, and complex-water qm interactions are accounted for implicitly in the diplr and ion protein-water interaction terms, thus yielding:

$$\Delta E_{bind} = \quad (7)$$
$$E^b_{r-l,vdw} + \Delta E_{(rl)-w,vdw} + E^b_{r-l,diplr} + \Delta E_{(rl)-w,dipir} + \Delta E_{w-w,hb,diplr} +$$
$$E^b_{r-l,ion} + \Delta E_{(rl)-w,ion} + \Delta E_{w-w,hb,ion} + E^b_{r-l,qm} + E^b_{r-w-l} + \Delta E_{tr}$$

where the self-energy of water is assumed to be dominated by water-water hydrogen bonding interactions (hb) and $\Delta E_{w-w,hb,diplr}$, and $\Delta E_{w-w,hb,ion}$ refer to changes in the self-energy of water due to the breaking of receptor-water and ligand-water diplr or ionic hydrogen bonding contacts, respectively, and the subsequent formation of bound state water-water hydrogen bonds.

Next, it is assumed van der Waals cancellation or that direct interchain vdw contacts formed at the receptor-ligand interface compensate for the receptor-water and ligand-water vdw contacts that are lost on complex formation ($E^b_{r-l,vdw} + E^b_{(rl)-w,vdw} - E^b_{r-w,vdw} - E^b_{l-w,vdw}) \approx 0$.

Similarly, it is assumed that the direct interchain diplr contacts formed at the receptor-ligand interface and any newly formed water-water H-bonds compensate for the free state receptor-water and ligand-water diplr (and qm) contacts that are lost on complex formation ($E^b_{r-l,diplr} + \Delta E_{w-w,hb,diplr} + \Delta E_{(rl)-w,diplr}) \approx 0$. The assumption of diplr and vdw cancellation implies, $$\Delta E_{bind} = E^b_{r-l,ion} + E^b_{r-l,qm} + E^b_{r-w-l} + \Delta E_{tr} + \Delta E_{solv} \quad (8)$$

where $$\Delta E_{solv} = \Delta E_{(rl)-w,ion} + \Delta E_{w-w,hb,ion} \quad (9)$$

Eqs. (8) and (9) give the change in the energy of complex formation. To obtain the binding free energy in water ($\Delta G_{bind}$), however, we must also consider the entropic contributions to binding:

$$\Delta G_{bind} = E^b_{r-l,ion} + E^b_{r-l,qm} + E^b_{r-w-l} + \Delta E_{tr} + \Delta E_{solv} - T\Delta S_{solv} - T\Delta S_{conf} - T\Delta S_{tr} \quad (10)$$

where $\Delta S_{solv}$ refers to changes in the entropy of solvent; $\Delta S_{conf}$ refers to changes in conformational entropy; and $\Delta S_{tr}$ refers to changes in the translational/rotational entropy. By collecting the energy terms with their corresponding entropy terms, a final and compact expression for the binding affinity can be written, $$\Delta G_{bind} = E^b_{r-l,ion} + E^b_{r-l,qm} + E^b_{r-w-l} T\Delta S_{conf} + \Delta G_{tr} + \Delta G_{solv} \quad (11)$$

Eq. (11) serves as the master thermodynamic equation and implies that the binding affinity is a function of the electrostatic and quantum-mechanical energy at the interface; the total energy of interfacial water mediated receptor-ligand interactions; the change in conformational entropy; the change in rotational and translational free energy and the free energy of desolvation.

Identifying Each Term in the Master Equation with a Physical Descriptor

To write $\Delta G_{bind}$ in terms of R, L and RL, each of the terms in Eq. (11) must be explicitly associated with a molecular property or physical descriptor characteristic of R, L, and RL. The simplest approach is to assume a linear relationship between each thermodynamic term and its corresponding physical descriptors. The equations describing the relationship between each term in Eq. (11) and its hypothesized descriptor are given below:

$$E^b_{r-l,ion} + E^b_{r-l,qm} = \alpha_{sb} X_{sb} + \alpha_{hb} X_{hb} \quad (12)$$

$$\Delta G_{solv} = \Delta E_{(rl)-w,ion} + \Delta E_{w-w,hb,ion} + \Delta S_{solv} \quad (13)$$
$$= \alpha_{+/-}(X_{RL,+/-} - X_{R,+/-} - X_{L,+/-}) +$$
$$\alpha_{s/c}(X_{RL,c/s} - X_{R,c/s} - X_{L,c/s})$$

$$-T\Delta S_{conf} = \alpha_{tor}(X_{RL,tor} - X_{R,tor} - X_{L,tor}) \quad (14)$$

$$E^b_{r-w-l} = \alpha_{gap} X_{gap} \quad (15)$$

$$\Delta G_{tr} = \varepsilon \quad (16)$$

In Eq. (12), $X_{sb}$ refers to the total number of salt bridges, defined as the difference between the total number of favorable and non-favorable electrostatic contacts at the interface and $X_{hb}$ refers to the total number of hydrogen bonds. Favorable contacts were defined for oppositely charged atoms separated by less than 4; unfavorable contacts were defined for like charges separated by less than 4. The nitro gen's of Lys and Arg side chains were assumed to carry positive charges, while the oxygen's of Glu and Asp chains were assumed to carry negative charges. Likewise, N-terminal nitrogen's, carboxyl oxygen's and phosphate oxygen's were all assumed to carry positive and negative charges, respectively. All hydrogen bonds were calculated according to the chemical, angle and distance criteria of Arthur Lesk (Gerstein (1992) *Acta Cryst A*48:271-276).

In Eq. (13), each $X_{i,+/-}$ refers to the total number of exposed charged groups, where i=RL, R or L. A group is counted as exposed if its solvent accessible surface area (SASA) is >1.0². Similarly, each $X_{i,c/s}$ refers to the total number of exposed hydrophobic groups (carbons or sulfurs). The change in the number of solvent exposed charged groups comprise the first two terms in Eq. (13), while the last two terms are estimated by the change in the number of solvent exposed hydrophobic groups.

The $X_{i,tor}$ terms in Eq. (14) refer to the total number of exposed side chain torsions including main-chain torsions for peptide ligands. All torsions associated with a side chain (or main chain in the case of peptides) possessing a relative SASA>60% were counted as exposed. All SASA calculations were made using the program NACCESS (Hubbard (1993) *Protein Sci* 3(12):2194-2206).

$X_{gap}$, (Eq. 15) refers to the gap volume at the interface and was calculated using SURFNET (Laskowski (1995) *J Mol Graph* 13(5):323-330, 307-328). In this calculation, a trial gap sphere is placed midway between the vdw surfaces of two neighboring atoms, and if any neighboring atoms penetrate the trial sphere, the radius is reduced until it just touches the penetrating atom. If the sphere radius falls below some pre-set radius the gap sphere is rejected, otherwise the final gap sphere is saved. The procedure is repeated for all atom pairs and the gap region is filled with spheres. Here, the default SURFNET values (minimum radius for a gap sphere=1.0; maximum radius=5.0) were used. It is also assumed that changes in translational/rotational free energy are constant ($\in$) in Eq. (16).

Using Regression to Parameterize the Function

Each $\alpha_i$ in Eqs. (12-16) is a proportionality constant that was determined by multiple linear regression. Regression assigns optimal $\alpha_i$'s to achieve a least-squares fit between a dependent variable (experimentally determined binding affinities) and a linear combination of independent variables (Eqs. (12-16)). Any disagreement between the estimated and experimental binding affinities is attributable to random error ($\mu$) which is assumed to be normally distributed with a constant variance, $\sigma^2$. The errors are further assumed to be independent of each other and each estimator X variable. Hence, multiple regression treats the $\alpha_i$'s as estimators of the true population coefficients ($\beta_i$'s), thus providing a basis for hypothesis testing and statistical inference. It is also assumed that no significant linear correlation exists between the independent variables (multi-colinearity).

Regression was used on a training set of 24 protein-protein and protein-peptide complexes. All 24 complexes were imported from the protein data bank using the molecular modeling package Deep View (Guex et al., (1997) *Electrophoresis* 18(15):2714-2723. The 24 complexes were pre-screened for acceptable experimental methodology (x-ray crystallography) and quality, according to resolution ($\leq 2.8$), r-factor ($\leq 0.25$), overall geometric quality, and receptor-ligand interface quality (visual inspection using Deep View by coloring the interface according to protein problems). Each header file was also manually inspected. All 30 training set complexes seem to satisfy the rigid-body body assumption as well. In constructing the test sets, the preceding quality criteria were not as rigorously applied. This compromise was necessary to construct test sets of adequate size and diversity.

For all training set structures and test set structures, the program REDUCE (Word et al., (1999) *Biochemistry* 35(16): 5109-5124) was used to flip and optimize HIS, ASN and GLN side chains. The PDB codes for all 30 training set complexes are summarized in Table 1. Using multiple linear regression, the final equation for predicting and explaining binding affinities was obtained:

$$\Delta G_{bind} = -0.82\Delta X_{+/-} + 0.064\Delta X_{c/s} - 0.6 X_{sb} - 0.93 X_{hb} - 0.0007 X_{gap} - 0.06\Delta X_{tor} - 0.36 \quad (17)$$

where $\Delta$ refers to the differences between the unbound and bound states.

Modifying Eq. (17) to Facilitate the Analysis of Transfer Free Energies

Below it is shown that the relationship between free energy estimates using Eq. (17) and similar estimates from other studies. One test compares side chain transfer free energies of a ligand (L) calculated using Eqs. (13, 17) with experimentally determined side chain transfer values from water (W) to octanol (O) obtained from a series of 8 (ac-Ala-X-Ala-t-butyl) tripeptides and 17 host-guest pentapeptides (Ac-WL-X-LL).

Typically, it is assumed that the ligand transfers at infinite dilution (i.e. no L-L interactions) and as a rigid body so that changes in the intramolecular energy and conformational entropy of the ligand can be ignored. Even with these simplifying assumptions, however, we would still be left with a complicated multi-term equation for the free energy of transfer ($\Delta G_{X,w-oct}$). Progress can be made, however, by recognizing that the charge desolvation and solvent entropy terms of Eqs. (13, 17) could be employed in a more complete equation for estimating water-octanol transfer free energies, $\Delta G_{X,w-oct}$. With this in mind, Eqs. (13) and (17) are readily modified for incorporation into an expression for $\Delta G_{X,w-oct}$, $$\Delta G_{X,w-oct} = -E_{l-w,ion} + \Delta E_{w-w,hb,ion} + \Delta S_{solv} + \Delta G_{other} \quad (18)$$

$$= -0.82 X_{L,+/-} + 0.064 X_{L,c/s} + f(X)$$

where the first term in Eq. (18) estimates the energetic cost of rupturing contacts between water and charged groups (charge desolvation) and the second term quantifies the favorable entropy changes in water that accompany hydrophobic group transfer; f(X) refers to any remaining free energy contributions that are not accounted for in Eq. (18) (changes in self-energy and entropy of octanol, for example); this term is dropped when making actual calculations.

It is important to keep in mind that Eq. (18) is only meant to estimate the charge desolvation and solvent entropy contributions to transfer. As such, it is unreasonable to assume that we can use it to fully predict and explain transfer free energies. However, if we observe a good correlation between experimentally determined values for $\Delta G_{X,w-oct}$ and the values predicted using Eq. (18), then this will give us confidence that Eqs. (13, 17, 18) do indeed capture the essential physics of charge-water interactions and solvent-entropy effects. Thus, by comparing predictions made using Eq. (18) with experimental side chain transfer free energies, we can test the functional form and coefficient magnitudes of Eqs. (13, 17).

In practice we used Eq. (18) to calculate the free energy of transferring a given ac-Ala-X-Ala-t-butyl tripeptide or Ac-WL-X-LL pentapeptide (ligand) from the aqueous phase to octanol. In making the calculations we assumed all tripeptide and pentapeptide atoms had an aqueous phase SASA>1.0 and an octanol phase SASA<1.0. Because $X_{L,+/-}$ and $X_{L,c/s}$ are calculated as negative (the change in the number of solvent exposed charged or hydrophobic atoms, respectively), the charged term makes an unfavorable contribution to transfer while the hydrophobic term makes a favorable one.

The contribution of individual side chains can also be calculated, $$\Delta\Delta G_{X,w-oct} = \Delta G_{X,w-oct} - \Delta G_{ref,w-oct} \quad (19)$$

where the reference amino acid (ref) was Gly in the case of the tripeptides and Ala in the case of the pentapeptides. The predicted $\Delta\Delta G_{X,w-oct}$ values calculated using Eqs. (18) and (19) can now be meaningfully compared with experimentally determined side chain free energies of transfer from water to n-octanol.

Computational Procedure for Mutant Construction

The program SCCOMP was used to construct all mutants (Eyal et al., (2004) *J Comput Chem* 25(5):712-724) SCCOMP models the side chains of mutated residues according to a scoring function that includes terms for complementarity (geometric and chemical), excluded volume, internal energy, and solvent accessible surface. In constructing the mutants, possible main-chain structural alterations were ignored.

Decoy Set Construction

To assess Eq. (17)'s ability to select out native from non-native binding modes, 9 decoy sets were constructed. The decoys were generated using the PatchDock docking server (Schneidman-Duhovny et al., (2005) *Nucleic Acids Res* 33 (Web Server issue):W363-367) which docks proteins according to shape complementarity. One hundred decoys were generated for each of nine complexes. The actual native-state complex was then added to each decoy set, for a total of 101 complexes. To insure that the PatchDock output included good near-native structures, the coordinates for the bound ligand and receptor were used in the docking runs.

To remove clashes from the docked complexes, the "move apart" option provided at the PatchDock website was used. Side chain conformations were optimized using SCWRL3.0 (Canutescu et al., (2003) *Protein Sci* 12(9):2001-2014). The complexes were then scored and ranked using Eq. (17).

Statistical Analysis

All statistical analyses were performed using Microsoft Excel and Sagata Regression Professional. Additional details on the statistical methods employed in this study can be found elsewhere (Jain et al., (2005) *FEBS Lett* 579(29):6659-6666).

Statistical Analysis of the Regression Model

The goodness-of-fit was evaluated between the function and the training set binding data. The extremely high correlation coefficient ($r=0.98$) demonstrates near optimal agreement between the binding energies estimated by Eq. (17) and the experimental values. The calculated coefficient of determination ($r^2=0.97$) implies that Eq. (17) accounts for roughly 97% of the variation in the experimental binding data, even when adjusted for the number of model descriptors ($r^2$-adj=0.96). The calculated root-mean-squared deviation (rmsd) between the implied and actual binding energies is $\approx RT$ and is negligible (rmsd=0.62 kcal·mol$^{-1}$). As a first, direct test of the predictive ability of the model, a leave-one-out cross validation was performed, yielding excellent results ($q^2=0.91$). Overall statistical significance (f-statistic) was calculated and the relevant null hypothesis tested ($\alpha_{+/-}=\alpha_{c/s}=\alpha_{sb}=\alpha_{hb}=\alpha_{gap}=\alpha_{tor}=0$). The null hypothesis was to be rejected for $p<0.05$. We obtained an f-statistic (89.6) and corresponding probability ($p<<\pm05$) that justified rejecting the null hypothesis and established Eq. (17) as a statistically significant estimator of the training set data. Next, the significance of each descriptor was evaluated by calculating t-statistics for each regression weight to test the null hypothesis, $\beta_i=0$, where i=+/−, c/s, sb, hb, gap, tor. The null hypothesis was to be rejected for $p<0.05$. It was determined that each of the six descriptors served as a significant estimator of the training set binding data.

If it can be shown that the underlying assumptions of regression have been satisfied, then the preceding statistical analysis is rigorously justified (Jain et al., supra). To test the assumption of multi-colinearity, a cross-correlation analysis was performed and revealed no significant correlations between the descriptors (data not shown). Variance inflation factors (VIF's) were also calculated which indicated a total absence of higher level correlations between the descriptors. To test the assumptions of error normality, independence, constant variance, zero mean, and linearity, plots of residuals versus predicted binding affinity and normals versus residuals were constructed (results not shown). As required, the residual-prediction plot exhibits a random distribution of points while the normal-residual plot exhibits approximate linearity. Our regression model thus satisfies the key assumptions of regression analysis and all inferences are justified accordingly.

As a final test, the values for each descriptor were transformed and the regression analysis was re-performed. The mathematical transformation involved subtracting the mean and dividing by the standard deviation for each of the six descriptors. Identical regression results were obtained for the transformed data as for the untransformed data (results not shown).

The main results of the statistical analyses are summarized in Tables 2 and 3. A plot of experimentally determined training set binding affinities versus empirical predictions ($\Delta G_{bind}$) is also provided in FIG. 1 (see Table 1 for data for all 24 training set complexes).

TABLE 1

Training Set PDB codes, Complex Types, Experimental and Predicted Binding Affinities

| PDB | Complex Type | Resolution ( ) | Rigid Body | $\Delta G_{bind,exp}$ | $\Delta G_{bind}$ |
|---|---|---|---|---|---|
| 1brs | Barnase/Barstar | 2.0 | | −17.3 | −17.8 |
| 1cho | Chymotrypsin/Ovomucoid | 1.8 | | −14.4 | −13.2 |
| 1cse | Subtilisin/Eglin C | 1.2 | | −13.1 | −14.0 |
| 1ppf | Elastase/Ovomucoid | 1.8 | | −13.5 | −13.9 |
| 1tec | Thermitase/Eglin C | 2.2 | | −14 | −14.0 |
| 2ptc | Trypsin/PTI | 1.9 | | −18.1 | −17.4 |
| 2sec | Proteinase/Inhibitor | 1.8 | | −14 | −13.8 |
| 2sic | Subtilisin/SSI | 1.8 | | −12.7 | −13.1 |
| 2sni | Subtilisin/C12 | 2.1 | | −15.8 | −15.4 |
| 3cpa | Carboxypeptidase A/Gly-Tyr | 2.0 | | −5.3 | −4.9 |
| 3sgb | Protease B/Ovomucoid | 1.8 | | −12.7 | −12.6 |
| 3tpi | Trypsinogen/PTI | 1.9 | | −17.3 | −18.2 |
| 4sgb | Protease B/PCI-1 | 2.1 | | −11.7 | −12.6 |
| 4tpi | Trypsinogen/Inhibitor | 2.2 | | −17.7 | −17.0 |
| 1vfb | Fv D1.3/Lysozyme | 1.8 | | −11.5 | −12.0 |
| 1yqv | Fab HyHel5/Lysozyme | 1.7 | | −14.5 | −13.4 |
| 2tpi | Trypsinogen/Ile-Val | 2.1 | | −5.8 | −6.2 |
| 2tgp | Trypsinogen/BPTI | 1.9 | | −17.8 | −17.5 |
| 1tpa | Trypsin/BPTI | 1.9 | | −17.8 | −17.4 |
| 2pcc | Cytochrome Peroxidase/Cyt C | 2.3 | 1cca (0.35), 1ycc(0.49) | −7 | −6.3 |

TABLE 1-continued

Training Set PDB codes, Complex Types, Experimental and Predicted Binding Affinities

| PDB | Complex Type | Resolution ( ) | Rigid Body | $\Delta G_{bind,exp}$ | $\Delta G_{bind}$ |
|---|---|---|---|---|---|
| 1acb | Chymotrypsin/Eglin C | 2.0 | 5cha (0.69), 1cse (0.63) | −13.1 | −13.5 |
| 1stf | Papin/Stefin B | 2.4 | 1ppn (0.32) | −13.5 | −13.4 |
| 1ycs | p53/53BP2 | 2.2 | 2ioo (0.69) | −10.3 | −11.3 |
| 1dhk | alpha-amylase/inhibitor | 1.9 | 1pif (1.28) | −14.3 | −14.5 |

In Table 1, "Rigid Body" refers to the status of the rigid-body approximation. A blank space indicates that the structure was used in past modeling work that assumes rigid-body binding and thus is assumed to satisfy the rigid-body approximation. For structures not used in past modeling studies the total Cα rmsd was calculated between bound and unbound receptor and ligand structures, respectively. It is assumed that the rigid body approximation is satisfied for Cα rmsd≦0.9. The unbound receptor PDB identifier is listed first and the ligand identifier is listed second; calculated rmsd values are given in parentheses. It was not always possible to find unbound receptor and ligand structures. Despite an rmsd of ≈1.28 1DHK was included in the training set and is assumed to satisfy the rigid body approximation (see text). The binding affinity data was collected from multiple sources (Gray et al., (2003) *J Mol Biol* 331(1):281-299; Horton et al., supra; Krystek et al., supra; Ma et al., supra, Vajda et al., supra, Weng et al., supra). All binding affinities are in kcal·mol$^{-1}$.

TABLE 2

Regression Diagnostics

| Descriptors[a] | α's | t stat | P-value | Lower 95% | Upper 95% | VIF[f] |
|---|---|---|---|---|---|---|
| E | −0.54 | — | — | — | — | — |
| $\Delta X_{+/-}$ | −0.85 | −10.91 | <0.0001 | −1.02 | −0.69 | 1.65 |
| $\Delta X_{c/s}$ | 0.067 | 5.60 | <0.0001 | 0.04 | 0.09 | 1.91 |
| $X_{sb}$ | −0.66 | −7.80 | <0.0001 | −0.84 | −0.48 | 2.45 |
| $X_{hb}$ | −0.90 | −15.14 | <0.0001 | −1.02 | −0.77 | 2.06 |
| $X_{gap}$ | −0.00087 | −3.98 | <0.0001 | 0.0013 | 0.0004 | 4.02 |
| $\Delta X_{tor}$ | −0.09 | −2.53 | 0.02 | −0.17 | −0.02 | 3.25 |

In Table 2, "descriptors" refers to a list of physical descriptors used in the regression model. α's refers to coefficients assigned to each descriptor by regression analysis. "t-stat" refers to t-statistic calculated from each descriptor. P-value refers to probability of getting a given t-statistic by chance (null hypothesis rejected for p<0.05). "Lower 95% refers to the confidence intervals for each regression coefficient. VIF refers to the Variance inflation factors. (see text).

TABLE 3

Regression Goodness-of-fit Analysis

| Statistic | Value |
|---|---|
| R | 0.98 |
| $R^2$ | 0.97 |
| $R^2$-adj | 0.96 |
| rmsd | 0.62 |
| f-test | 89.6 |
| p-value | <<0.00001 |
| $Q^2$ | 0.91 |

In Table 3, R is the correlation coefficient; $R^2$ is the coefficient of determination and $R^2$-adj is the coefficient of determination adjusted for the number of regressors. The rmsd gives the root mean squared deviation between the binding affinities estimated from Eq. 11 and the experimentally determined ones (kcal·mol$^{-1}$). An f-test and corresponding probability was calculated to test the overall significance of the regression model (null hypothesis rejected, p<0.05). As an initial test of Eq. 11's predictive power, a leave-one-out analysis was performed and $Q^2$ calculated.

While even the most exhaustive statistical analysis cannot, definitively establish physical causation, our analysis strongly suggests that casual connections exist between the physical descriptors of Eq. (17) and experimentally determined binding affinities.

Evaluating the Descriptors

Each of the physical descriptors in Eq. (17) has been identified with a specific thermodynamic quantity, as indicated in Eqs. (12-16): the formation of salt bridges and hydrogen bonds at the receptor-ligand interface, the burial of hydrophobic and charged groups to form roughly complimentary surfaces, and the burial and immobilization of side chain torsions. Each of these phenomena is thought to be important to complex formation (Jones et al., (1996) *Proc Natl Acad Sci USA* 93(1):13-20. Nevertheless, the physics of each a priori association was evaluated by comparing the results to those from previous modeling and experimental work.

I. vdw and diplr cancellation. It is assumed that the interchain vdw and diplr energy at the interface balances the favorable receptor-solvent and ligand-solvent vdw, and diplr contacts lost on complex formation, $$E^b_{r-l,vdw} = -\Delta E_{(rl)-w,vdw} \quad (20a)$$

$$E^b_{r-l,diplr} = -\Delta E_{(rl)-w,diplr} - \Delta E_{w-w,hb,diplr} \quad (20b)$$

where $\Delta E_{(rl)-w,diplr}$ implicitly includes qm contributions and thus hydrogen bonding interactions with the solvent ($\Delta E_{(rl)-w,diplr} = \Delta E_{(rl)-w,hb}$).

The hypothesis of vdw cancellation holds that receptor and ligand atoms will pair up at the interface so as to offset the loss in favorable receptor-water and ligand-water vdw energy that accompanies complex formation. Therefore, the term on the right of Eq. (20a) is reasonably assumed to be positive and it follows that the $E^b_{r-l,vdw} < 0$. This provides a necessary but not sufficient condition of vdw cancellation since $E^b_{r-l,vdw}$ must be just negative enough to exactly offset $\Delta E_{(rl)-w,vdw}$.

It is reasonable to hypothesize that native state protein-protein binding modes minimize $E^b_{r-l,vdw}$ and that this grounds vdw cancellation. In fact, the physicochemical characteristics of protein-protein interfaces suggest that, for a given ligand primary structure, $E^b_{r-l,vdw}$ is indeed being minimized with respect to non-biological binding modes, and that this leads to vdw cancellation. Structural studies indicate that biological protein-protein interfaces are clash-free, wellpacked, involve numerous hydrophobic contacts, and exhibit a high degree of geometric complementarity (Jones et al., supra; Lo Conte et al., (1999) J Mol Biol 285(5):2177-2198. Such interfaces will have highly favorable interchain vdw energy, especially with respect to other possible but non-biological binding interfaces. Indeed, these facts have been recognized by some researchers as justifying the assumption of vdw cancellation (Gatchell et al., (2000) Proteins 41(4): 518-534). The fact that interfaces represent relatively low dielectric media and are characterized by extensive hydrophobic contacts also suggests that the vdw contacts formed at the interface will be energetically more favorable than the receptor-water and ligand-water contacts that are lost on association. Thus, there exists a solid physicochemical basis for assuming that, relative to the large number of possible interfaces, biological interfaces minimize $E^b_{r\text{-}l,vdw}$ and negate $\Delta E_{r\text{-}l\text{-}w,vdw}$.

Next, the hypothesis of diplr cancellation is considered. Stated concisely, diplr cancellation requires that the dipole-dipole and charge-dipole receptor-ligand interactions formed at the interface, along with any newly formed water-water hydrogen bonds, are sufficient to compensate for the favorable receptor-water and ligand-water hydrogen bonds (diplr+qm) that are lost on complex formation. If the diplr interactions include a qm component (if they are hydrogen bonds), this will provide additional stabilizing energy to the complex.

The formation of a single receptor-ligand hydrogen bond will make the term on the right of Eq. (20b) positive; it follows that $E^b_{r\text{-}l,diplr}<0$. This provides a necessary condition for diplr cancellation. However, $E^b_{r\text{-}l,diplr}$ must be sufficiently negative to exactly offset $\Delta E_{(rl)\text{-}w,hb}$. Like in the case of vdw cancellation, we hypothesize that native state protein-protein binding modes minimize $E^b_{r\text{-}l,diplr}$ and that this leads to diplr cancellation. Once again, it was found that the physicochemical characteristics of biological interfaces are consistent with this hypothesis.

Protein-protein interfaces are characterized by a large number of polar-polar and polar-charged contacts. Moreover, the relatively low dielectric constant of a protein all but guarantees that, everything else being equal, these electrostatic interactions will be stronger than the protein-water interactions that are lost on complex formation. Numerous studies employing various methods indicate that biological protein-protein interfaces exhibit considerable charge-charge or electrostatic complementarity. A recent study even suggests that the partial charges on ligands and receptors are electrostatically optimized for one another (Sulea et al., (2003) Biophys J 84(5):2883-2896. Thus, the empirical data suggests the receptor binding pocket and its cognate ligand are physically adapted to minimize $E^b_{r\text{-}l,diplr}$ and negate $\Delta E_{r\text{-}l\text{-}w,hb}$.

Finally, the success of docking algorithms that rely on simple geometric and electrostatic based scoring strategies, especially scoring functions that combine geometric and electrostatic complementarity, lends further support to the hypothesis of vdw-diplr minimization/cancellation. Indeed, the hypothesis provides a way to rationalize the success of such simple scoring strategies, especially when it comes to the scoring and ranking improvements observed with combined geometric/electrostatic scoring functions.

II. Salt bridge and hydrogen bond descriptors. Salt bridges can contribute favorably or unfavorably to the electrostatic energy, depending on the relative number of favorable to unfavorable ionic contacts. Hydrogen bonds, however, are predicted to always contribute favorably to the binding energy. In terms of magnitude, salt bridges will contribute $\approx-0.66$ kcal·mol$^{-1}$, while hydrogen bonds will contribute $\approx-0.90$ kcal·mol$^{-1}$ in qm energy. Experimental work on complex formation between adenine and synthetic nucleotide receptors indicates that the enthalpy of hydrogen bond formation in water is $\approx-0.8$ kcal·mol$^{-1}$ (Kato et al., (1995) Proc Natl Acad Sci USA 92(4):1208-1212) and poly-alanine α-helix folding experiments in water show the enthalpy of hydrogen bond formation is $\approx-0.9$ kcal·mol$^{-1}$ (Baldwin (2003) J Biol Chem 278(20):17581-17588). To see how this fits with the model estimate for the qm energy of an interfacial hydrogen bond, it was assumed that diplr cancellation or that the bound state polypepetide CO—HN electrostatic interaction energy, combined with the energy of additional water-water H-bonds, is sufficient to compensate for the peptide-water hydrogen bonds of the free state that are lost during the course of the reaction. The total binding energy is then given by, $\Delta E_{bind}=E^b_{r\text{-}l,qm}$. From Eq. (17), $E^b_{r\text{-}l,qm}-0.90$ kcal·mol$^{-1}$. Thus, the model estimate is in excellent agreement with experiment. The preceding calculation provides justification for the regression estimated H-bonding coefficient and for the assumption of diplr cancellation.

A second argument lends further support to our model estimate for $E^b_{r\text{-}l,qm}$. According to quantum calculations, the gas phase interaction energy of a peptide hydrogen bond is $\approx-6.6$ kcal·mol$^{-1}$ to $-7.4$ kcal·mol$^{-1}$ (Martin et al., (1999) Nat Struct Biol 6(5):403-406), and recent work suggests hydrogen bonds are $\approx 10\%$ covalent. This leads to a low estimate of $E^b_{r\text{-}lqm}\approx-0.66$ kcal·mol$^{-1}$ and a high estimate of $E^b_{r\text{-}lqm}\approx-0.74$ kcal·mol$^{-1}$. Both estimates set a range that is in reasonable agreement with our estimate of 0.90 kcal·mol$^{-1}$.

Unlike the case for the H-bond coefficient, it was not possible to locate any experimental evidence to directly evaluate the salt bridge contribution to the electrostatic energy of binding. A simple argument from electrostatics, however, suggests that $\approx-0.6$ kcal·mol$^{-1}$ is nonetheless physically reasonable. Consider two oppositely charged atoms, with identical partial charges of 0.5, separated by R=4.0, immersed in a medium of 100 mM NaCl and interacting through a protein with dielectric, D=12-24 (Olson et al., (2000) Proteins 38(1): 115-119; Warshel et al., (2006) Biochim Biophys Acta 1764 (11):1647-1676). By Coulomb's law, the two atoms will possess an electrostatic interaction energy in the range $\approx-0.58$-1.15 kcal·mol$^{-1}$. Hence, the Eq. (17) value of $\approx-0.6$ kcal·mol$^{-1}$ is reasonable. Moreover, the coefficients and form of Eq. (17) imply that receptor-ligand salt-bridge formation can be overall stabilizing or destabilizing, depending on the presence or absence of hydrogen bonds, the payment of a desolvation penalty and changes in conformational entropy. This is an important observation that is consistent with the results of studies which indicate stabilizing and destabilizing effects for salt-bridges (Sheinerman et al., (2002) Curr Opin Struct Biol 10(2):153-159; Xu et al., supra).

III. Side chain burial and conformational entropy descriptors. In Eq. 17, complex formation is opposed by changes in conformational entropy which is directly related to the number of side-chain and (main-chain in the case of peptide ligands) torsions buried at the interface. However, Eq. (17) implies that torsion burial opposes complex formation by $\approx 0.091$ kcal·mol$^{-1}$ which is much smaller than the 0.6-0.5 kcal·mol$^{-1}$ value typically employed. More recently, Hu and Kulhman (2006), Proteins 62(3):739-748, arrived at a range of magnitudes, from $\approx 0.09$ kcal·mol$^{-1}$ per torsion (Val) to $\approx 0.22$ kcal·mol$^{-1}$ per torsion (Met). Moreover, Krystek et al. (supra) acknowledged that their 0.6 kcal·mol$^{-1}$ term probably overestimates the side chain entropy contribution.

A final calculation might prove helpful on this point. The Krystek entropy estimate for 1CHO ($-T\Delta S_{conf}$=30 kcal·mol$^{-1}$) entails that the unbound receptor and ligand can sample $\approx 5.0\times10^{21}$ times as many isoenergetic conformational states as the complex, while our estimate for 1CHO ((-TΔ-$S_{conf}$=2.1 kcal·mol$^{-1}$) entails that the unbound receptor and ligand can sample ≈33 times as many states as the complex.

IV. The solvent (solv) descriptor. Eq. (18) predicts that the transfer of charged groups from water to n-octanol is unfavorable by 0.85 kcal·mol$^{-1}$ and the transfer of hydrophobic groups is favorable by 0.0674 kcal·mol$^{-1}$. Moreover, according to the present model, the energetics of transfer varies according to the number of charged and hydrophobic groups that undergo transfer rather than the total amount of charged and hydrophobic surface area that is transferred. This separates the present invention from most popular approaches.

Eq. (18) was evaluated quantitatively by comparing predicted peptide transfer free energies with experimentally determined peptide water-octanol transfer free energies. It is important to keep in mind that Eq. (18) is only intended to estimate charge desolvation energies and water entropy changes. Furthermore, Eq. (18) was not parameterized on water-octanol transfer data, but on protein-protein binding data. Hence, while absolute agreement between experiment and theory is unlikely a good correlation between experiment and prediction will do much to establish the physical and theoretical soundness of Eq. (18), and by implication Eq. (17), and its transferability.

Octanol is thought to provide a reasonable model of protein cores and interfaces, although this has been debated (Dill (1990) Biochemistry 29(31):7133-7155; Juffer et al., (1995) Protein Sci 4(12):2499-2509). Hence, experimentally determined side-chain octanol-water transfer free energies provide a benchmark test for a proposed function like Eq. (18). Typically, the transfer data is obtained using amino acid analogs and is reported in terms of individual side chain contributions. A drawback of using such data, however, is that it does not include contributions from the flanking peptide bonds. This situation is remedied by using transfer data for eight guest side chains (X) in host-guest (ac-Ala-X-Ala-t-butyl) tripeptides (Kim et al., (1992) Pharm Res 9(4):504-514; Wimley et al., (1996) Biochemistry 35(16):5109-5124) and seventeen guest side chains (X) in host-guest pentapeptides (Ac-WL-X-LL) (Wimley et al., supra).

Figure 2:
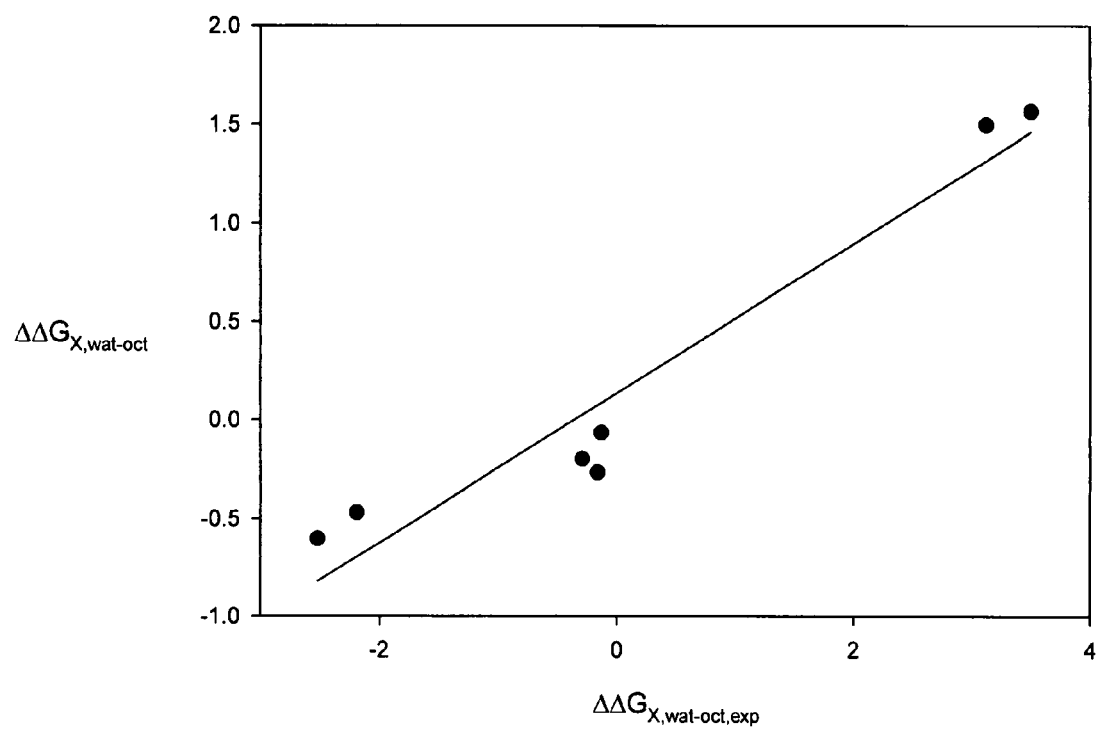
FIG. 2 shows predicted water-octanol ($\Delta\Delta G_{X,w-oct,p}$) versus experimental water-octanol ($\Delta\Delta G_{X,w-oct}$) transfer free energies (kcal·mol$^{-1}$) for eight host-guest (X) tripeptides using data from eqs. (18) and (19); $r^2$=0.93; rmsd=1.36 kcal·mol$^{-1}$.
Figure 3:
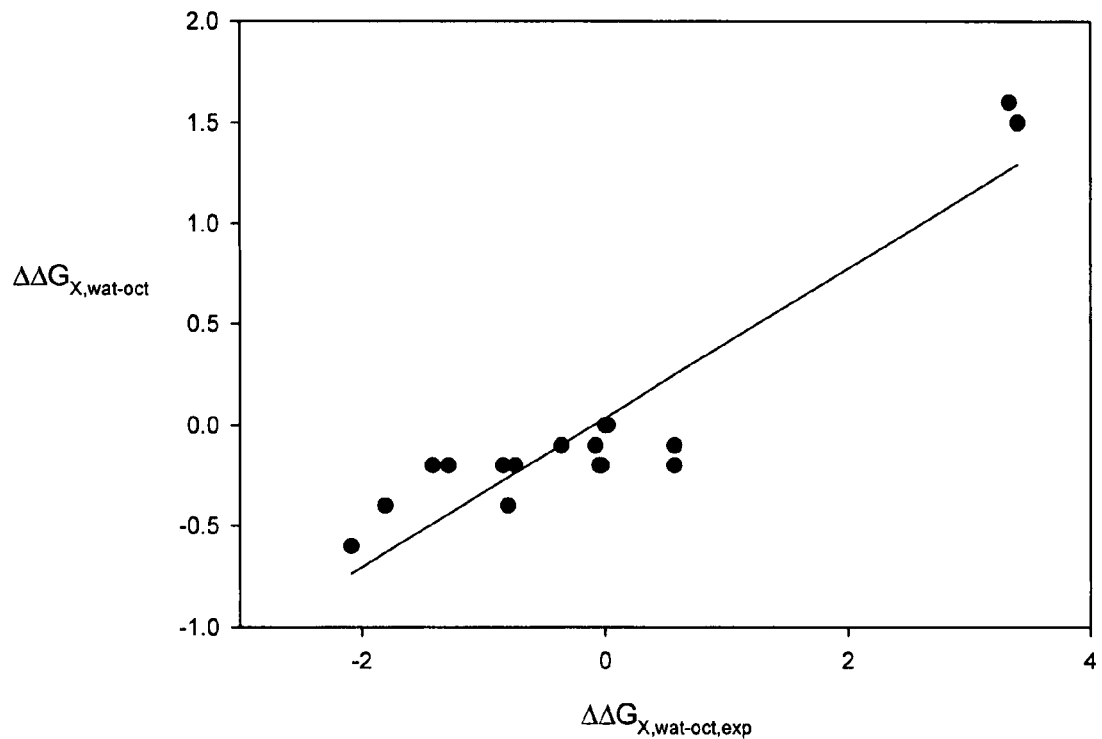
FIG. 3 shows predicted water-octanol ($\Delta\Delta G_{X,w-oct,p}$) versus experimental water-octanol ($\Delta\Delta G_{X,w-oct}$) transfer free energies (kcal·mol$^{-1}$) for 17 host-guest (X) pentapeptides using data from eqs. (18) and (19); $r^2$=0.86 and rmsd=0.97 kcal·mol$^{-1}$.

Eqs. (18) and (19) were used to calculate water-interface transfer free energies for all 8 (tripeptide) side chains and quantitatively compared the results with the experimental water-octanol side chain data of Kim and Szoka (supra). The results of the comparison are summarized in FIG. 2. The high correlation coefficient (0.97), coefficient of determination (0.93) and low rmsd (1.36 kcal·mol$^2$) shows excellent agreement. Such a result is remarkable, especially given the simplicity of Eq. (18) and the fact that it was parameterized on protein binding data. More specifically, the high correlation provides compelling evidence that the signs and magnitudes of the charge transfer (-0.85 kcal·mol$^{-1}$) and hydrophobic transfer (0.067 kcal·mol$^{-1}$) contributions to Eq. (18) are physically accurate. The high correlation coefficient also validates our substituting a "change in exposed groups" calculation for a "change in surface area" calculation. The same analysis using the data for the 17 host-guest pentapeptides was performed. The Lys and Arg side chains were eliminated from the analysis because they were shown to form intramolecular salt bridges during the transfer experiments. The results of the analysis are summarized FIG. 3. As shown in FIG. 3, the high correlation coefficient (0.93) and low rmsd (0.97 kcal·mol$^{-1}$) provides additional support for the inference that Eq. (18) accurately estimates the charge desolvation and solvent-entropy contributions to $\Delta G_{X,w\text{-}oct}$ and for the use of solvent-exposed group enumeration in place of surface area calculations. Additional arguments and evidences can also be adduced in support of our model for $\Delta G_{X,w\text{-}oct}$.

A simple enumeration of CH bonds and the total number of carbons provides a better explanation for the results of hydrocarbon transfer experiments and the hydrophobic effect more generally, than do surface area calculations (Kyte (2003) Biophys Chem 100(1-3):193-203; Matulis (2001) Biophys Chem 93(1):67-82). Likewise, the number of —$CH_2$— and —$CH_3$ groups was found to correlate better with protein mutant stability changes than were changes in surface area (Jackson (1993) J Mol Biol 276(1):265-285). These studies support our methodology of estimating $\Delta G_{X,w\text{-}oct}$ by simply enumerating changes in the number of exposed groups.

Polar but uncharged side chains, when flanked by peptide bonds, often have a higher affinity for n-octanol than do the same side chains of amino acid analogues. In addition, the transfer free energy for Ala (0.87 kcal·mol$^{-1}$) is virtually indistinguishable from that of Ser (0.85 kcal·mol$^{-1}$) and very close to that of His (0.92 kcal·mol$^{-1}$) and Thr (0.95 kcal·mol$^{-1}$). Thus, the experimental evidence suggests that many polar but uncharged side chain groups do not incur a net desolvation penalty and that polar group transfer is readily accommodated by octanol. To explain this behavior, it has been suggested that the flanking peptide bonds reduce side chain polarity (Wimley et al., supra). Presumably, these observations and conclusions would only be strengthened if octanol were replaced by a slightly more polar medium i.e. the protein-protein interface. More recently it has even been argued, on experimental and theoretical grounds, that polar groups may even pay a negligible desolvation penalty on transfer from water to the protein interior due to the nonspecific but tight packing of the core (Pace (2001) Biochemistry 40(2):310-313). Theory and experiment thus indicate that many polar groups have an equal affinity for n-octanol as for water and that the same can be expected for the protein core. All of this can be interpreted in support of the assumption of diplr cancellation.

The energetics of polar group transfer to octanol (and the interface), however, is complicated by the drastic difference between the transfer free energies observed for Tyr (-0.8 kcal·mol$^{-1}$ and Phe (-1.81 kcal·mol$^{-1}$) and the fact that we have not considered peptide group nitrogen's and oxygen's in our analysis. A simple explanation, one consistent with the prior art and the assumption of diplr cancellation, for the Ala, Ser, His, Thr, Phe, Tyr data, is that the peptide bond has a distant-dependent attenuating effect on the polarity of side chain polar groups.

V. The gap volume descriptor. $X_{gap}$ is the gap volume (or void volume) in Å$^3$ at the interface of two molecular entities. The gap volume term in Eq. (17) is thought to estimate $E^b_{r\text{-}w\text{-}l}$ such that the interaction energy in the bound state arising from water bridged R and L groups is directly proportional to the gap volume at the interface. These contacts are long-ranged and encompass charge-charge, charge-dipole, dipole-dipole and induced-dipole interactions. If we hypothesize that the gap regions at the interface are filled with solvent, then $E^b_{r\text{-}w\text{-}l}$ is directly proportional to the total number of water bridging molecules present in gap regions at interface.

According to Eq. (17) $E^b_{r\text{-}w\text{-}l}$ is stabilizing by about -0.00087 kcal·mol$^{-1}$ for every Å$^3$ of interfacial gap volume. If we assume the gap regions are filled with roughly spherical water molecules and if we adopt the polar and apolar atom-atom contact definitions and corresponding water radii (1.97-2.59 Å) suggested by Williams et al., (1994) Protein Sci 3(8):1224-1235, then $E^b_{r-w-l}$ is stabilizing by ≈−0.024 and −0.05 kcal·mol$^{-1}$ per water molecule in a gap region (a water molecule occupies roughly 32-73 Å$^3$). Thus, according to Eq. (17) the barnase-barstar complex (1BRS), with a gap volume of 2662 Å$^3$ or 37-80 waters, is stabilized by, $E^b_{r-w-l}$≈−2.31 kcal·mol$^{-1}$.

VI. Evaluating the assumption of a constant $\Delta G_{tr}$. Complex formation is accompanied by a change in the translational/rotational free energy, $\Delta G_{tr}$, which can be decomposed into energetic $\Delta E_{tr}$ and entropic $\Delta S_{tr}$ contributions. Modeling studies typically treat $\Delta S_{tr}$ as making a constant contribution to the binding reaction and fail to explicitly treat $\Delta E_{tr}$. Recent experimental work, however, indicates that changes in $\Delta E_{tr}$ are important and that for protein binding reactions in water and at T=298K, $\Delta G_{tr}$≈0±0.6 kcal·mol$^{-1}$ (Yu et al., (2001) Biophys J 81(3):1632-1642). This experimental quantity is in good agreement with our regression estimate, $\Delta G_{tr}$=∈=−0.54 kcal·mol$^{-1}$.

Evaluating the Predictive Power of the Invention

Figure 4:
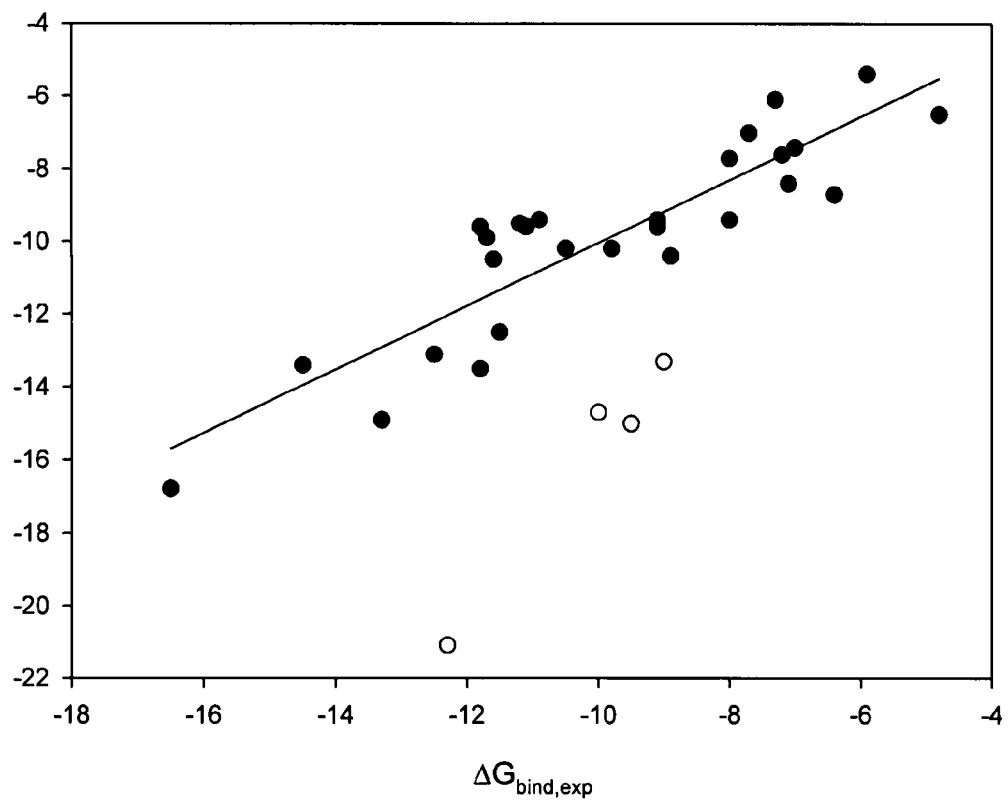
FIG. 4 shows predicted ($\Delta G_{bind}$) versus experimental ($\Delta G_{bind,exp}$) binding affinities for a 35 member test set. All predictions were made using Eq. (17); units are kcal·mol$^{-1}$; see Table 2 for test set data and binding free energies; $r^2$=0.79; r=0.89 rmsd=1.20 kcal·mol$^{-1}$.

The leave-one-out cross validation results suggests Eq. (17) is predictive. The function was used to blindly predict binding affinities on a test set of 35 protein-protein and protein-peptide complexes (see the table below). Experimental and predicted binding affinities are summarized in Table 4 and FIG. 4.

Abbreviations used in Table 4 are the same as those used in Table 1 above. Despite rmsd's of ≈1.8 and 2.4, 1fwp and 1ebp were included in the test set and are assumed to satisfy the rigid body approximation (see text). The "?" indicates that clear independent evidence for the truth or falsity of the rigid-body approximation could not be determined (see text). The last four entries resulted in failed predictions.

Evaluating the Discriminative Power of the Invention

Eq. (17) was evaluated for its ability to discriminate between native and native-like binding modes and non-native ones. A function with perfect discriminative power would always place native binding modes in free energy minima, native-like binding modes at higher points on the free energy surface and non-native binding modes at still higher points on the free energy surface. A total of 101 binding modes, including the experimentally determined native-state binding mode, were scored and ranked for 9 complexes (Table 5).

TABLE 5

Rank Of Native State And Native-Like Complexes Out of 100 Decoy Complexes Generated Using Patchdock

| PDB | Complex | Native Rank | Native-like Rank$^c$ | Native-like RMSD$^d$ |
|---|---|---|---|---|
| 1BRS | E-EI | 1 | 2 | 1.10 |
| 1CHO | P-PI | 6 | 2 | 0.72 |
| 1BRC | P-PI | 1 | 9 | 0.82 |
| 1CSE | P-PI | 9 | —$^e$ | — |

TABLE 4

Test Set PDB codes, Complex Types, Experimental and Predicted Binding Affinities

| PDB | Complex Type | Resolution (Å) | Rigid Body | $\Delta G_{bind,exp}$ | $\Delta G_{bind}$ |
|---|---|---|---|---|---|
| 1a0o | CheY/ChA | 3.0 | 1ehc(0.72), fwp(1.8) | −8.1 | −7.6 |
| 1hbs | Deoxyhemoglobin | 3.0 | (Xu et al., 1997a) | −4.8 | −6.5 |
| 2iff | Antibody/Lysozyme | 2.7 | (Weng et al., 1997) | −11.1 | −9.6 |
| 1avz | V-1 Nef/Fyn Sh3 | 3.0 | 1avv(0.68), 1shf(0.42) | −6.4 | −8.7 |
| 1hhg | MHC/Peptide | 2.6 | (Rognan et al., 1999) | −8.9 | −10.4 |
| 1hhh | MHC/Peptide | 3.0 | (Rognan et al., 1999) | −11.6 | −10.5 |
| 1hhi | MHC/Peptide | 2.5 | (Rognan et al., 1999) | −11.2 | −9.5 |
| 1hhk | MHC/Peptide | 2.5 | (Rognan et al., 1999) | −10.9 | −9.4 |
| 1lcj | Sh2/pTYR | 1.8 | (Zhou and Abagyan, 1998) | −8.0 | −9.4 |
| 1lck | Sh3-Sh2/pTYR | 2.5 | (Zhou and Abagyan, 1998) | −7.0 | −7.4 |
| 1lkl | Sh2/pTYR | 1.8 | (Zhou and Abagyan, 1998) | −8.0 | −7.7 |
| 1sps | Sh2/pTYR | 2.7 | (Zhou and Abagyan, 1998) | −9.1 | −9.6 |
| 1tce | Sh2/pTYR | nmr | (Zhou and Abagyan, 1998) | −5.9 | −5.4 |
| 2pld | Sh2/pTYR | nmr | (Zhou and Abagyan, 1998) | −9.1 | −9.4 |
| 1irs | IRS-1 PTB/pTYR | nmr | (Zhou and Abagyan, 1998) | −7.2 | −7.6 |
| 1shc | PTB/pTYR | nmr | (Zhou and Abagyan, 1998) | −10.0 | −7.9 |
| 1sha | Sh2/pTyr | 1.5 | (Zhou and Abagyan, 1998) | −7.6 | −7.1 |
| 1dkz | DNAK/Peptide | 2.0 | (Kasper et at., 2000) | −9.1 | −9.5 |
| 2er6 | Endothiapepsin/peptide | 2.0 | 1oew(0.6) | −9.8 | −10.2 |
| 1bbz | Sh3/peptide | 1.7 | (Palencia et al., 2004) | −7.7 | −7.0 |
| 1ebp | EPO receptor/peptide | 2.8 | 1ern(2.14) | −11.7 | −9.9 |
| 1nsn | Antibody/Nuclease | 2.8 | (Lo Conte et al., 1999) | −11.8 | −13.5 |
| 1jhl | Antigen/Antibody | 2.4 | (Lo Conte et al., 1999) | −11.8 | −9.6 |
| 1mda | Dehydrogenase/Amicyanin | 2.5 | ? | −7.3 | −6.1 |
| 3hfm | Hy/HEL-10/FAB-Lysozyme | 3.0 | (Lo Conte et al., 1999) | −13.3 | −14.9 |
| 1bth | Thrombin/BPTI | 2.3 | ? | −16.5 | −16.8 |
| 2kai | Kallikrein A/BPTI | 2.5 | (Weng et al., 1997) | −12.5 | −13.1 |
| 2jel | Jel42 FAB/Hpr | 2.5 | (Mintseris et al., 2005) | −11.5 | −12.5 |
| 1gla | IIIGLC/Glycerol Kinase | 2.6 | 1f3g(0.42) | −7.1 | −8.4 |
| 1mel | VH Antibody/Lysozyme | 2.5 | Lo Conte | −10.5 | −10.2 |
| 1bql | Anti-HEL FAB/Lysozyme | 2.6 | 1bql(0.0), 1dkj(0.84) | −14.5 | −13.4 |
| 1nmb$^b$ | NC10/Neuraminidase | 2.2 | (Lo Conte et al., 1999) | −10.0 | −14.7 |
| 1avw$^b$ | Trypsin/STI | 1.8 | (Lo Conte et al., 1999) | −12.3 | −21.1 |
| 1wej$^b$ | E8 Antibody/Cytochrome C | 1.8 | 1qbl(0.91), 1hrc(0.36) | −9.5 | −15.0 |
| 1hhj$^b$ | MHC/Peptide | 2.5 | (Rognan et at., 1999) | −9.0 | −13.3 |

TABLE 5-continued

Rank Of Native State And Native-Like Complexes Out of 100 Decoy Complexes Generated Using Patchdock

| PDB | Complex | Native Rank | Native-like Rank[c] | Native-like RMSD[d] |
|---|---|---|---|---|
| 1VFB | AbAg | 6 | — | — |
| 1YQV | AbAg | 21 | 13 | 3.00 |
| 1UGH | Misc | 1 | 3 | 2.29 |
| 1HHG | PP | 1 | 4 | 0.12 |
| 1BBZ | PP | 2 | 5 | 2.00 |

In Table 5, E-EI is enzyme-enzyme inhibitor, P-PI is protease-protease inhibitor, AbAg is antibody-antigen, Misc is miscellaneous, PP is protein-peptide. Native Rank refers to the rank of the experimentally determined native state complex in terms of binding free energy (a rank of 1 implies that the native complex had the lowest binding free energy out of all 101 complexes tested). Native-like Rank refers to the rank, in terms of binding free energy, of the best native-like complex (to qualify as native-like, rmsd≦3.0). Native-like RMSD refers to rmsd of best native-like complex; "–" indicates that Patchdock failed to identify a native-like structure.

The results in Table 5 indicate that Eq. (17) can be used to rank native and native-like solutions in the top 13 for all 9 complexes tested, assuming a native-like binding mode has a Cα rmsd≦3.0. For 6 of the complexes, Eq. (17) was used to rank the native and native-like solutions $1^{st}$ or $2^{nd}$.

The method of the invention can be implemented in any fashion, but is preferably implemented as a computer algorithm on a pair of molecular entities (e.g., proteins and/or peptides) as follows.

(1) Obtain a protein-protein or protein-peptide structure. This can be an experimentally determined structure (x-ray crystallography or NMR) or a computer generated structure (protein docking) using known methods. Values for each of the relevant variables are then determined.

(2) Run the algorithm of Eq. (17) on the structure and obtain a predicted free energy of binding ($\Delta G_{bind}$). The sign (positive or negative) and magnitude of this value permits one to predict the binding affinity between proteins and/or peptides. If $\Delta G_{bind}$<0, it is predicted that the two molecular entities will spontaneously form a complex. In this case; the more negative $\Delta G_{bind}$, the stronger the association between the molecular entities. If $\Delta G_{bind}$=0, it is predicted that the two molecular entities are just as likely to form a complex as remain in the unbound state. If $\Delta G_{bind}$>0, it is predicted that the two molecular entities will not spontaneously form a complex.

It is possible to test this prediction by determining experimentally whether the molecular entities really do form a complex and to what extent they form a complex. It is also possible to calculate an experimental $\Delta G_{bind}$ and compare it to the value calculated by implementing the method of the invention. When the method of the present invention is used, there is a strong correlation between the $\Delta G_{bind}$ values calculated and the experimental values, as shown in Table 4.

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A method, for execution on a computing device, of predicting the binding affinity between a first molecular entity and a second molecular entity, wherein the first molecular entity or the second molecular entity comprises a protein or a peptide, comprising the steps of:

(1) calculating the free energy of binding $\Delta G_{bind}$ between said first molecular entity and said second molecular entity according to the following equation:

$$\Delta G_{bind} = -0.82\,\Delta X_{+/-} + 0.064\Delta X_{c/s} - 0.6X_{sb} - 0.93X_{hb} - 0.0007X_{gap} - 0.06\Delta X_{tor} - 0.36$$

wherein $\Delta G_{bind}$ is given by a linear combination consisting of seven terms including a constant and six terms each having a coefficient and a distinct one of six parameters $\Delta X_{+/-}$, $\Delta X_{c/s}$, $X_{sb}$, $X_{hb}$, $X_{gap}$, $\Delta X_{tor}$, where $X_{+/-}$ is the total number of exposed charged groups;
$X_{c/s}$ is the total number of exposed hydrophobic groups;
$X_{sb}$ is the total number of salt bridges;
$X_{hb}$ is the total number of hydrogen bonds;
$X_{gap}$ is the gap volume at the interface of said first molecular entity and said second molecular entity;
$X_{tor}$ is the total number of exposed side chain torsions;
and wherein Δ refers to the difference between the bound and unbound states;

(2) evaluating said free energy of binding to predict the binding affinity between said first molecular entity and said second molecular entity; and (3) outputting said evaluation to a user in a user-readable format;

wherein said calculating, said evaluating and said outputting steps are performed with the computing device, the computing device being configured to perform said steps.

2. The method of claim 1, wherein said protein or peptide is wild type.

3. The method of claim 1, wherein said protein or peptide is a mutant.

4. The method of claim 3, wherein said mutant comprises one or more amino acid substitutions.

5. The method of claim 3, wherein said mutant comprises one or more amino acid deletions.

6. The method of claim 1 wherein said second molecular entity comprises a protein or peptide.

7. The method of claim 6, wherein said protein or peptide is wild type.

8. The method of claim 6, wherein said protein or peptide is a mutant.

9. The method of claim 8, wherein said mutant comprises one or more amino acid substitutions.

10. The method of claim 8, wherein said mutant comprises one or more amino acid deletions.

11. The method of claim 1, wherein said user-readable format is a computer display.

* * * * *